(12) United States Patent
Materer et al.

(10) Patent No.: US 8,077,316 B2
(45) Date of Patent: Dec. 13, 2011

(54) CHLORINE DIOXIDE SENSOR

(75) Inventors: Nicholas Materer, Stillwater, OK (US);
Allen Apblett, Stillwater, OK (US);
Dane Scott, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 316 days.

(21) Appl. No.: 12/372,978

(22) Filed: Feb. 18, 2009

(65) Prior Publication Data
US 2010/0208239 A1 Aug. 19, 2010

(51) Int. Cl.
*G01N 21/00* (2006.01)
(52) U.S. Cl. .................. 356/436; 356/437
(58) Field of Classification Search ............ 422/62, 422/105, 111, 119, 91, 80, 82.05, 83, 90; 250/343, 282, 286, 287, 288; 68/5 R; 423/477, 423/478; 436/125, 171; 356/432–442
See application file for complete search history.

(56) References Cited

U.S. PATENT DOCUMENTS

| | | |
|---|---|---|
| 3,306,156 A | 2/1967 | Glasser et al. |
| 4,152,073 A | 5/1979 | Zimmerman |
| 4,251,224 A | 2/1981 | Cowley et al. |
| 4,251,503 A | 2/1981 | Swindells et al. |
| 4,311,485 A | 1/1982 | Saltzman et al. |
| 5,283,199 A | 2/1994 | Bacon, Jr. et al. |
| 5,382,520 A | 1/1995 | Jenson et al. |
| 6,304,327 B1 * | 10/2001 | Campbell et al. ......... 356/437 |
| 7,119,891 B2 | 10/2006 | White et al. |
| 2004/0062683 A1 | 4/2004 | Yam et al. |
| 2004/0233447 A1 | 11/2004 | White et al. |
| 2005/0194546 A1 * | 9/2005 | Saccomanno ......... 250/461.1 |
| 2006/0237657 A1 | 10/2006 | Gamiles et al. |

FOREIGN PATENT DOCUMENTS

| | | |
|---|---|---|
| DE | 602 16 988 T2 | 10/2007 |
| JP | 2008157874 | 7/2008 |
| WO | 9953297 | 10/1999 |

OTHER PUBLICATIONS

"Data Sheet for 9187sc Amperometric Chlorine Dioxide Sensor", published 2005 by Hach Company.
"Technical Information regarding Chlorine/Chlorine Dioxide Measurement OCM223", Technical Information No. TI 214e00 No. 51503822, published by Hobeco Sudamericana Ltda, Rio de Janeiro, Brazil.
Australian Patent Office PCT International Search Report, International Application PCT/US2009/043594, mailed Sep. 10, 2009.
Australian Patent Office PCT Written Opinion of the ISA, International Application PCT/US2009/043594, Mailed Sep. 10, 2009.

* cited by examiner

*Primary Examiner* — Gregory J Toatley
*Assistant Examiner* — Tri T Ton
(74) *Attorney, Agent, or Firm* — Fellers, Snider, Blankenship, Bailey & Tippens, P.C.

(57) ABSTRACT

A chemical sensor is disclosed. The sensor has a test chamber for receiving chemicals in a gaseous state, the test chamber having two substantially transparent windows at first and second ends of the test chamber. The sensor uses a pulse operated ultraviolet light emitting diode at the first end of the test chamber emitting at a wavelength close to a maximum in the absorption band of a test chemical, and an electromagnetic sensor at a second end of the test chamber, the sensor being sensitive to the light emitted by the light emitting diode.

13 Claims, 3 Drawing Sheets

CHLORINE DIOXIDE SENSOR

FIELD OF THE INVENTION

This disclosure relates to the field of noxious gas detection, and more specifically, to detection of gaseous chlorine dioxide.

BACKGROUND OF THE INVENTION

Currently available commercial sensors exist for monitoring or measuring the concentration of chlorine dioxide. However, many of these sensors are developed for regulatory applications which require measurements at very low concentration levels (e.g., parts per billion). At higher concentrations and long exposure durations, existing electrochemical based sensors can be damaged such that they will become inaccurate or inoperative. Additionally, for some applications, the sensor needs to be able to operate accurately at high relative humidity.

What is needed is a system and method for addressing the above, and related, issues.

SUMMARY OF THE INVENTION

The invention of the present disclosure, in one aspect thereof, comprises a chemical sensor. The sensor has a test chamber for receiving chemicals in a gaseous state, the test chamber having two substantially transparent windows at first and second ends of the test chamber. A pulse operated ultraviolet light emitting diode is at the first end of the test chamber, emitting at a wavelength close to a maximum in the absorption band of a test chemical. An electromagnetic sensor is at a second end of the test chamber, the sensor being sensitive to the light emitted by the light emitting diode.

In one embodiment, the pulsed light emitting diode is modulated at about 1 kilohertz to increase the signal-to-noise ratio at the electromagnetic sensor. The electromagnetic sensor may be a photodiode. In one embodiment, the photodiode is sensitive to radiation at a wavelength of about 370 nanometers.

The windows may comprise a material that is resistant to degradation in the presence of chlorine dioxide. The window may comprise a material that is resistant to degradation in the presence of chlorine dioxide at relative humidities above 70%. In one embodiment, the windows material is polyethylene terephthalate (PET). In another embodiment, the windows comprise fluorinated ethylene propylene (FEP).

The pulsed ultraviolet light emitting diode may operate in an on state for about 50 milliseconds per pulse and may remain in an off state for about 5 seconds between pulses.

The test chamber may be elongated and have an inlet port and an outlet port. In some embodiments, a beam splitter interposes the pulsed ultraviolet light emitting diode and the window at the first end of the test chamber. The beam splitter directs a portion of the electromagnetic radiation from the ultraviolet light emitting diode to a reference diode and passes a remainder of the radiation into the test chamber.

DETAILED DESCRIPTION OF THE PREFERRED EMBODIMENTS

Figure 1:
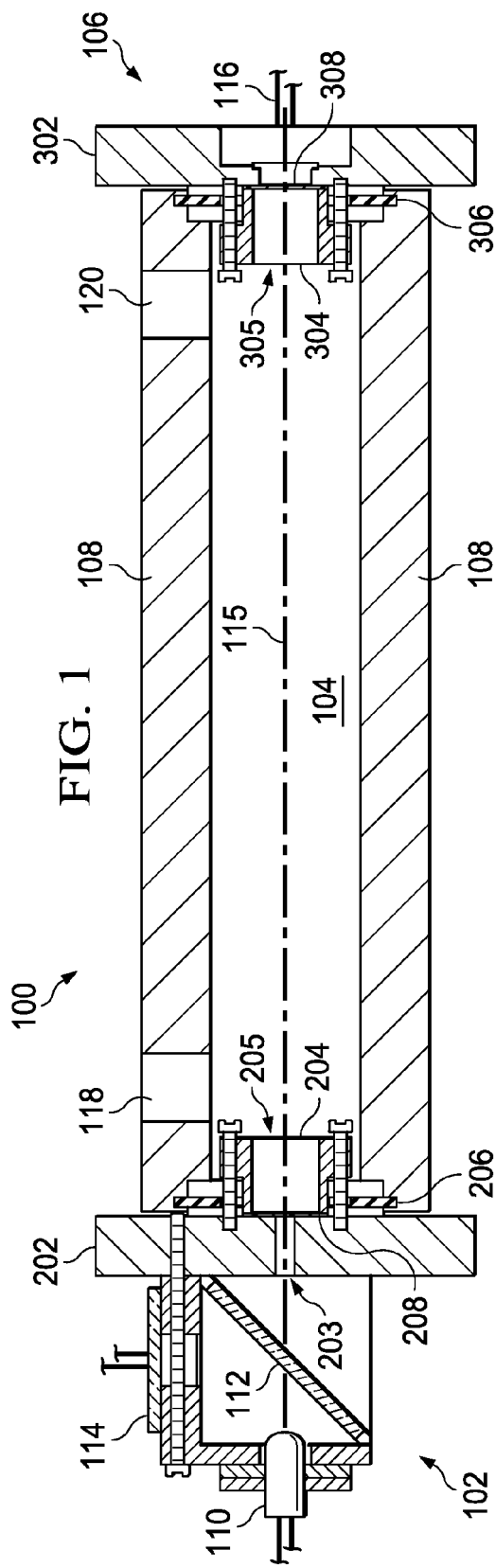
FIG. 1 is a cross-sectional view of one embodiment of a chlorine dioxide sensor according to aspects of the present disclosure.

Referring to FIG. 1, a cross-sectional view of one embodiment of a chlorine dioxide ($ClO_2$) sensor according to aspects of the present disclosure is shown. The chlorine dioxide sensor 100 is designed to detect chlorine dioxide in a gaseous state. Quantification may be achieved for minute (parts per billion) quantities up to very high concentrations. A test chamber 104 is defined by one or more test chamber walls 108. Although the view of FIG. 1 is a cross-sectional view, it will be appreciated that there may be four walls 108 providing a rectangular test chamber 104. In other embodiments, the test chamber 104 may be tubular and the walls 108 may represent a single tubular circumferential wall surrounding the test chamber 104. At opposite ends of the test chamber 104 are a source end 102 and a detector end 106.

In the present embodiment, an ultraviolet light emitting diode (UV LED) is provided for energizing the test chamber 104. The presence of chlorine dioxide and/or the concentration thereof is determined by spectrographic analysis of the sample in the test chamber 104. In the present embodiment, the UV LED 110 provides a beam of electromagnetic energy in the ultraviolet wavelength region. The beam is split by a beam splitter 112 that may comprise a quartz plate. A portion of the energy from the UV LED 110 may be directed by the beam splitter 112 to a reference diode 114. The remainder of the energy from the UV LED 110 that is not reflected to the reference diode 114 will pass from the source end 102 through the test chamber 104 to the detector end 106. The path of the beam is illustrated by line 115. The detector end 106 is equipped with a detector diode 116.

In operation, the UV LED 110 will be active or illuminated in a pulsed fashion. Illuminating the test chamber 104 in a pulsed or periodic fashion will minimize photochemical reactions with chlorine dioxide within the test chamber 104. In one embodiment, the UV LED 110 will be periodically activated. For example, activation for about 50 milliseconds approximately every 5 seconds. To increase the signal-to-noise of the detected radiation, the UV LED 110 can also be modulated at frequencies in the kilohertz range (e.g., about 1 to about 10 kilohertz).

The UV LED 110 may provide electromagnetic radiation generally toward the ultraviolet portion of the spectrum but other wavelengths of light could be present in the beam as well. In the particular embodiment shown, the UV LED 110 will at least transmit around the wavelength of 370 nanometers. Both the reference diode 114 and the detector diode 116 will be sensitive to radiation at this wavelength. In this manner, the reference diode 114 may be activated to indicate that the UV LED 110 is active. Furthermore, the reference diode 114 may be used to compensate for any intensity variations in the output of the UV LED 110.

Due in part to the corrosive and photochemical effects that may occur with chlorine dioxide, the test chamber walls 108, as well as any other components of the sensor 100 that come in contact with chlorine dioxide, will need to be made of a material that is suitably resilient to the effects of chlorine dioxide. The materials may also be resistant to the effects of chlorine dioxide in a high humidity environment (e.g., above 70% relative humidity). In one embodiment, the components may comprise polyethylene terephthalate (PET). In another embodiment, the components may comprise fluorinated ethylene propylene (FEP). PET and FEP are two examples of materials that would be suitable to construct the sensor 100.

It is contemplated that the sensor 100 may be installed and used more or less continuously for an indeterminate period of time. In the embodiment shown, one or more of the test chamber walls 108 will define opening 118, 120 for introduction of test gases into the test chamber 104 and for removal of the tested sample. In one embodiment, it is contemplated that gas flow through the test chamber will be more or less continuous In one embodiment, the source end 102 comprises the UV LED 110, the beam splitter 112, and the reference diode 114. The construction of the beam splitter 112 in combination with the UV LED 110 and reference diode 114 may attach to an end plate 202. The end plate 202 may define a first end of the test chamber 104. The end plate 202 in the present embodiment is comprised of aluminum.

The end plate 202 may define a passage 203 to allow passage of the beam from the UV LED 110. A film holder 204, which may comprise PET, attaches against the end plate 202. The film holder also defines a passage 205. Retained by the film holder 204 is a thin film 208. In the present embodiment, the thin film 208 comprises PET. The thin film 208 may comprise high-purity PET having a thickness of about 0.004 inches. A high purity film of PET that is sufficiently thin will not interfere substantially with the optics and operation of the sensor 100. The thin film 208 provides a substantially transparent window into the test chamber 104. As described, the components of the sensor 100 coming in contact with the sample, which may include chlorine dioxide, must be made from a resilient material. Thus, the end plate 202 is protected by the film 208 and the film holder 204.

An O-ring 206 may be provided to seal the end of the test chamber 104. The O-ring may comprise a fluorocarbon elastomer such as Viton®. Viton® will be less resilient against the corrosive effects of the chlorine dioxide than those components comprising PET. However, the Viton® will adequately seal the test chamber 104 and will be somewhat protected from the chlorine dioxide by the configuration of the end 102 of the sensor 100. It can be seen that the end plate 202 and film holder 204 project inward to the chamber 104 against the walls 108. This will prevent the O-ring 206 from being in the primary gas flow during operation and will serve to decrease the corrosive effects of the chlorine dioxide.

The detector end 106 comprises another end plate 302, which also positions the detector diode 116 in the center of the beam path 115. The end plate 302 may comprise aluminum. Attached on the outside of the end plate 302 is the detector diode 116. An end cap 304 attaches to the inside of the end plate 302. The end cap 304 may comprise PET and define a passage 305. The end cap also protects the end plate 302 from coming in contact with the sample, which may include chlorine dioxide. The passage 305 allows for maximum transmission of the test beam from the test chamber 104 to the detector diode 116. In some embodiments, the end cap 304 retains another thin film 308 against the end plate 302 and the photodiode 116. This film 308 may also comprise high purity PET having thickness of about 0.004 inches. This will allow the beam to exit the test chamber 104 and reach the detector diode 116 substantially unaffected. The thin film 308 provides a substantially transparent window into the test chamber 104.

As before, a Viton® O-ring 306 is provided to seal the end 106 of the sensor 100. The configuration of the second end 106 of the sensor 100 will keep the O-ring 306 out of the main gas flow and serve as some protection against the corrosive effects of the chlorine dioxide on the O-ring.

The detector diode 116 is configured to detect absorption around the ultraviolet absorbance maximum of the chlorine dioxide spectra. Thus, the LED beam traveling from the UV LED 110 through the test chamber 104 and striking the detector diode 116 will have been altered in the presence of chlorine dioxide gas. This alteration may present itself in the form of a loss in intensity of the test beam.

As can be seen in FIG. 1, various plastic screws may be used to hold the major components of the sensor 100 in place. In one embodiment, the assembly screws will be nylon. However, in other embodiments, the components may be assembled and epoxied or glued in place. For example, the walls 108 may be epoxied together and against the end plates 202, 302. The film holder 204 and end cap 304 may also be epoxied in place against the insides of the end plates 202, 302, respectively.

Figure 2:
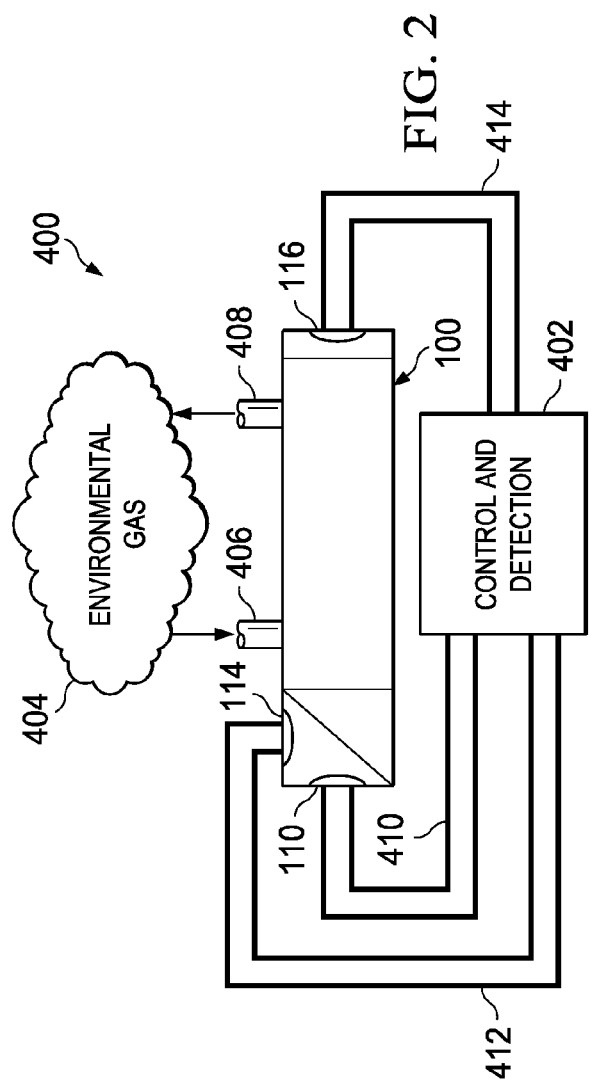
FIG. 2 is a schematic view of the chlorine dioxide sensor of FIG. 1 with attached control and detection circuitry.

Referring now to FIG. 2, a schematic diagram of the chlorine dioxide sensor of FIG. 1 with attached control and detection circuitry 402 is shown. The control and detection circuitry 402 provides power and control to the UV LED 110 as needed. The control and detection circuitry 402 connects to the UV LED 110 via wire leads 410. The control and detection circuitry 402 connects to the reference diode 114 and the detector diode 116 via wire leads 412 and 414, respectively.

The detection circuitry 402 may read and/or compare the output from the LEDs 114, 116 to determine whether there is a significant absorption that would be indicative of chlorine dioxide within the test chamber. The concentration of chlorine dioxide in the test chamber 104 may also be discernable. In one embodiment, detection and control circuitry may comprise one or more integrated circuits and/or discrete analog or digital components.

The functionality of the circuitry 402 could also be provided in software operating on a general purpose computer or integrated circuit. In addition, the circuitry 402 may provide the necessary signal conditioning and amplification to ensure adequate and usable readings from the diodes 114, 116. The output from the circuitry 402 may be an analog voltage or a digital reading. In some embodiments, the circuitry 402 will be equipped to log or record readings for later retrieval.

In one embodiment, the photocurrent of the detector diode 116 will be measured by the circuitry 402. A change in photocurrent of the detector diode 116 may correspond to the presence and/or concentration of chlorine dioxide. Enhanced signal-to-noise ratio may be obtained at the detector circuit 402 by modulating the UV LED 110 at several kilohertz. In some embodiments, the reference diode 114 will measure the output of the UV LED 110 to correct for possible variations in the output of the UV LED 110. The photocurrent of the reference diode 114 will be proportional to the output of the UV LED 110 regardless of the presence of chlorine dioxide because the UV light incident on the reference diode 114 will not pass through the test chamber.

In FIG. 2, environmental gas is shown as a cloud 404. The environmental gas 402 may be ambient atmosphere that is to be tested for chlorine dioxide. The gas 402 may also be the output or input of a specific process for which monitoring is desired. In some embodiments, a conduit or input port 406 may be provided for delivering the test sample to the sensor 100. An outlet conduit or port 408 may be provided for exhausting the tested sample. In some embodiments, the ports 406, 408 provide a continuously refreshed test sample into the openings 118, 120 (FIG. 1) of the test chamber. Positive pressure and/or vacuum may be used depending upon the needs of the user.

Figure 3:
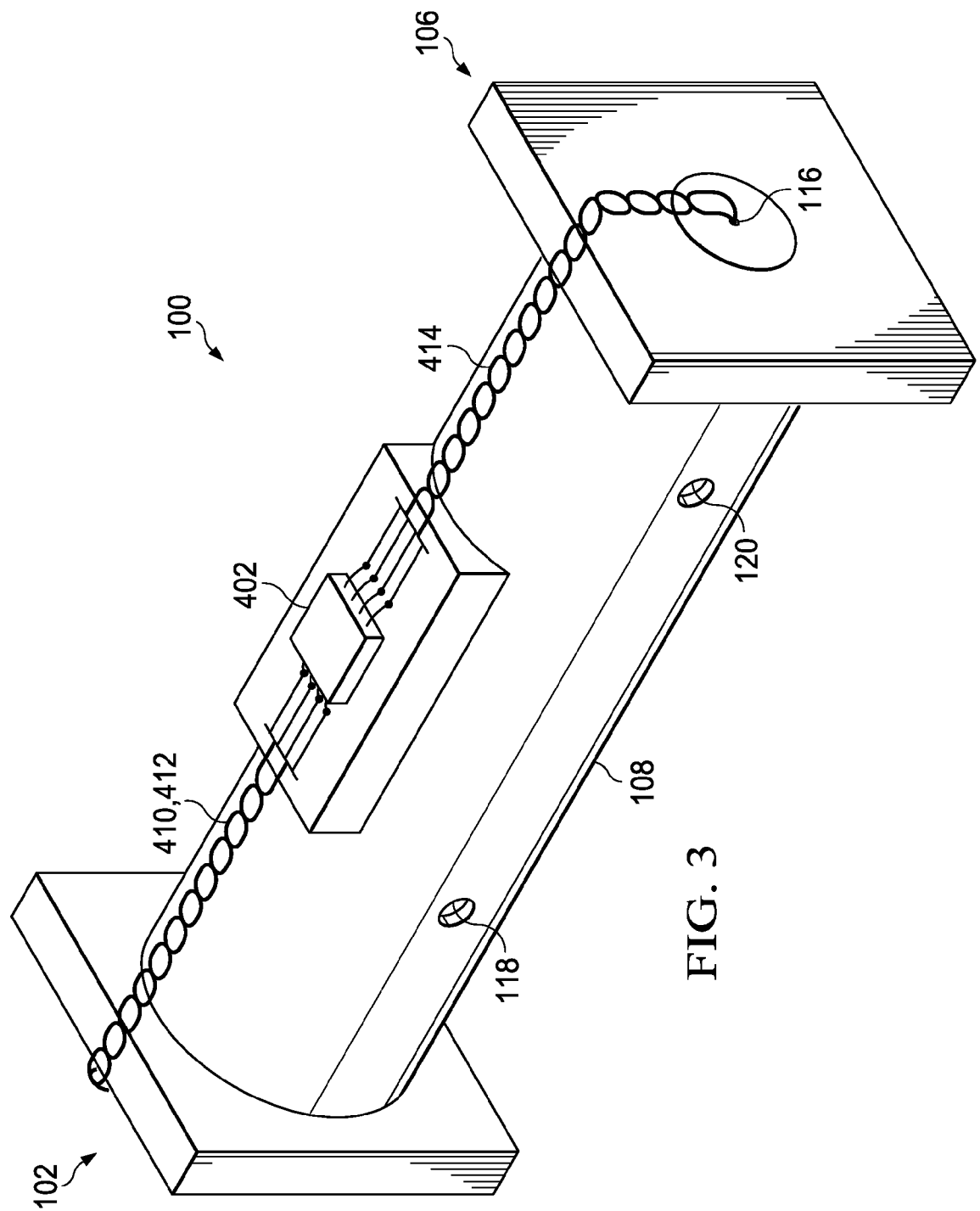
FIG. 3 is a perspective view of the chlorine dioxide sensor of FIG. 1 with attached control and detection circuitry.

Referring now to FIG. 3, a perspective view of the chlorine dioxide sensor of FIG. 1 with attached control and detection circuitry is shown. Here, the overall physical shape of the sensor 100 can be seen. In the embodiment shown, the test chamber is defined in part by a single cylindrical wall 108. The detection and control circuitry 402 has been mounted to the wall 108 outside the test chamber. The leads 414 connecting the control circuitry 402 to the detector diode 116 can be seen leading to the detector end 106 of the sensor 100. Similarly, the leads 410, 412 connecting the circuitry 402 to the UV LED 110 and the reference diode 114, respectively, can also be seen leading to the source end 102.

Figure 4:
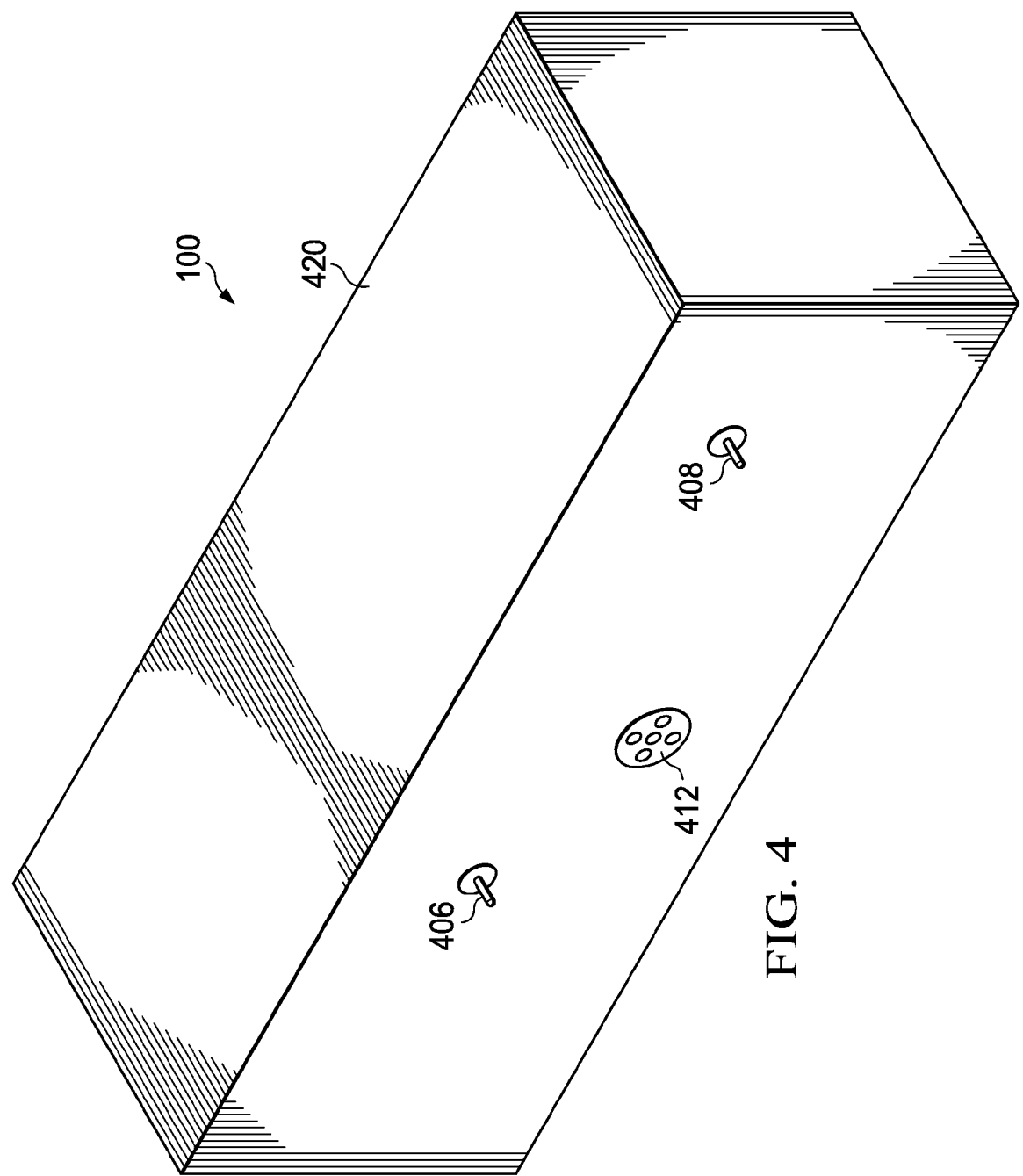
FIG. 4 is a perspective view of the chlorine dioxide sensor of FIG. 1 with an opaque enclosure.

Referring now to FIG. 4, a perspective view of the chlorine dioxide sensor of FIG. 1 with an opaque enclosure 420 is shown. Due to the detrimental photochemical reactions that are possible with chlorine dioxide, the test chamber 104 may need to be shielded from ambient light. Depending upon the wavelength of the ambient light, the diodes 114, 116 may also benefit from shielding. The detection electronics may also benefit from shielding to reduce possible electromagnetic interferences. In the present embodiment, an opaque casing 420 has been fitted around the entire sensor 100. In order to provide test samples to the sensors 100, ports 406, 408 are provided in communication with the openings 118, 120 of the wall 108 of the test chamber 104. Using positive pressure and/or vacuum, a continuous or intermittent test sample may be provided. In order to power the circuitry 402 and to read the output or results of the test, a communication and power port 412 may be provided. The enclosure 420 itself may comprise an appropriate metal, plastic, or other material of suitable opacity and resiliency to the environment in which the sensor 100 will be used.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A chemical sensor comprising:
   a test chamber for receiving chemicals in a gaseous state, the test chamber having two substantially transparent windows at first and second ends of the test chamber;
   an ultraviolet light emitting diode at the first end of the test chamber emitting at a wavelength close to a maximum in the absorption band of a test chemical and operating in a pulsed fashion to minimize photochemical reactions of the test chemical; and
   an electromagnetic sensor at a second end of the test chamber, the sensor being sensitive to the light emitted by the light emitting diode and detecting absorption of the light emitted around the maximum in the absorption band of the test chemical.

2. The chemical sensor of claim 1, wherein the pulsed light emitting diode is modulated at about 1 kilohertz to increase the signal-to-noise ratio at the electromagnetic sensor.

3. The chemical sensor of claim 1, wherein the windows comprise a material that is resistant to degradation in the presence of chlorine dioxide.

4. The chemical sensor of claim 1, wherein the window comprises a material that is resistant to degradation in the presence of chlorine dioxide at relative humidities above 70%.

5. The chemical sensor of claim 1, wherein the windows comprise polyethylene terephthalate (PET).

6. The chemical sensor of claim 1, wherein the windows comprise fluorinated ethylene propylene (FEP).

7. The chemical sensor of claim 1, wherein the pulsed ultraviolet light emitting diode operates in an on state for about 50 milliseconds per pulse.

8. The chemical sensor of claim 7, wherein the pulsed ultraviolet light emitting diode remains in an off state for about 5 seconds between pulses.

9. The chemical sensor of claim 1, wherein the test chamber is elongated and has an inlet port and an outlet port.

10. The chemical sensor of claim 1, further comprising:
    a beam splitter interposing the pulsed ultraviolet light emitting diode and the window at the first end of the test chamber; and
    a reference photodiode;
    wherein the beam splitter directs a portion of the electromagnetic radiation from the ultraviolet light emitting diode to the reference diode and passes a remainder of the radiation into the test chamber.

11. The chemical sensor of claim 1, wherein the electromagnetic sensor at the second end of the test chamber is a photodiode.

12. The chemical sensor of claim 1, wherein the electromagnetic sensor at the second end of the photodiode is sensitive to radiation at a wavelength of about 370 nanometers.

13. A chemical sensor comprising:
    a test chamber for receiving chemicals in a gaseous state, the test chamber having two substantially transparent windows at first and second ends of the test chamber;
    a pulse operated ultraviolet light emitting diode at the first end of the test chamber emitting at a wavelength close to a maximum in the absorption band of a test chemical;
    an electromagnetic sensor at a second end of the test chamber, the sensor being sensitive to the light emitted by the light emitting diode;
    a beam splitter interposing the pulsed ultraviolet light emitting diode and the window at the first end of the test chamber; and
    a reference photodiode;
    wherein the beam splitter directs a portion of the electromagnetic radiation from the ultraviolet light emitting diode to the reference diode and passes a remainder of the radiation into the test chamber.

* * * * *